(12) United States Patent
Braun et al.

(10) Patent No.: US 11,166,741 B2
(45) Date of Patent: Nov. 9, 2021

(54) EXPANDABLE SCAFFOLDS FOR SUBMUCOSAL TISSUE SEPARATION

(71) Applicant: Boston Scientific Scimed, Inc., Maple Grove, MN (US)

(72) Inventors: Johnathan Braun, Shoreview, MN (US); Selina Merkling, St. Louis Park, MN (US); Kimberly Robertson, Forest Lake, MN (US); Matthew Frost, Watertown, MN (US); Daniel Gregorich, Plymouth, MN (US); Adam Huot, Maple Grove, MN (US); John Hingston, Framingham, MA (US); Oscar R. Carrillo, Jr., Middletown, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 293 days.

(21) Appl. No.: 15/387,729

(22) Filed: Dec. 22, 2016

(65) Prior Publication Data

US 2017/0181764 A1  Jun. 29, 2017

Related U.S. Application Data

(60) Provisional application No. 62/271,418, filed on Dec. 28, 2015.

(51) Int. Cl.
| | |
|---|---|
| *A61B 17/32* | (2006.01) |
| *A61B 17/34* | (2006.01) |
| *A61B 17/00* | (2006.01) |
| *A61B 90/00* | (2016.01) |

(52) U.S. Cl.
CPC .. *A61B 17/320016* (2013.01); *A61B 17/3478* (2013.01); *A61B 17/3468* (2013.01);
(Continued)

(58) Field of Classification Search
CPC ... A61B 2090/0815–0816; A61B 2017/00269; A61B 17/12022–12195;
(Continued)

(56) References Cited

U.S. PATENT DOCUMENTS

| | | | | |
|---|---|---|---|---|
| 5,749,894 A | * | 5/1998 | Engelson | A61B 17/12022 128/898 |
| 6,723,108 B1 | * | 4/2004 | Jones | A61B 17/12022 606/151 |

(Continued)

OTHER PUBLICATIONS

M. Khashab, et al. "Pilot study of 'Scissorhands' technique for gastric endoscopic submucosal dissection using novel gel and endoscopic scissors in a porcine model (with video)," Digestive Endoscopy, (2014), vol. 26, pp. 365-368.

*Primary Examiner* — Darwin P Erezo
*Assistant Examiner* — Brigid K Byrd
(74) *Attorney, Agent, or Firm* — Kacvinsky Daisak Bluni PLLC

(57) ABSTRACT

The present disclosure relates to the field of endoscopy. Specifically, the present disclosure relates to systems and methods for en bloc resection of malignant and pre-malignant lesions and/or tumors within the gastrointestinal (GI) tract. More specifically, the present disclosure relates to systems and methods for delivering an expandable scaffold between tissue layers (e.g., between the muscularis and submucosa layers) to elevate and stabilize the lesion or tumor for fast and efficient resection.

17 Claims, 9 Drawing Sheets

(52) U.S. Cl.
CPC ............... *A61B 2017/00269* (2013.01); *A61B 2017/00818* (2013.01); *A61B 2017/320044* (2013.01); *A61B 2090/0815* (2016.02)

(58) Field of Classification Search
CPC ........ A61B 17/12181; A61B 17/12186; A61B 17/1214–12145; A61B 17/12159; A61B 17/3478; A61B 10/0233; A61B 2017/00818; A61B 2017/1205; A61F 2/95–97; A61F 5/003; A61F 5/0069–5/0073; A61F 5/0013; A61M 29/00–2029/025
See application file for complete search history.

(56) References Cited

U.S. PATENT DOCUMENTS

| | | | |
|---|---|---|---|
| 7,909,809 B2 | 3/2011 | Scopton et al. | |
| 9,668,690 B1* | 6/2017 | Imran | A61N 1/0517 |
| 2005/0107823 A1* | 5/2005 | Leone | A61B 17/12022 |
| | | | 606/200 |
| 2006/0070631 A1* | 4/2006 | Scopton | A61B 17/3478 |
| | | | 128/898 |
| 2006/0142789 A1* | 6/2006 | Lehman | A61B 17/00234 |
| | | | 606/153 |
| 2006/0149307 A1* | 7/2006 | Durgin | A61B 17/00234 |
| | | | 606/191 |
| 2007/0260178 A1* | 11/2007 | Skerven | A61B 17/3478 |
| | | | 604/96.01 |
| 2009/0069806 A1* | 3/2009 | De La Mora Levy | A61B 17/221 |
| | | | 606/46 |
| 2011/0022149 A1* | 1/2011 | Cox | A61B 17/12181 |
| | | | 623/1.11 |
| 2011/0060308 A1* | 3/2011 | Stokes | A61F 5/0013 |
| | | | 604/500 |
| 2014/0316012 A1* | 10/2014 | Freyman | A61L 31/146 |
| | | | 514/772.3 |

* cited by examiner

EXPANDABLE SCAFFOLDS FOR SUBMUCOSAL TISSUE SEPARATION

CROSS-REFERENCE TO RELATED APPLICATIONS

This application claims the benefit of priority from U.S. Provisional Application No. 62/271,418, filed on Dec. 28, 2105, the entirety of which is incorporate by reference herein.

FIELD

The present disclosure relates to the field of endoscopy and specifically, to systems and methods for en bloc resection of malignant and pre-malignant lesions within the gastrointestinal (GI) tract. In particular, the present disclosure relates to systems and methods for delivering an expandable scaffold between tissue layers (e.g., between the muscularis and submucosa layers) to elevate and stabilize the lesion for fast and efficient resection.

BACKGROUND

Endoscopic procedures such as endoscopic mucosal resection (EMR) and endoscopic submucosal dissection (ESD) are commonly performed to detect and remove malignant and pre-malignant lesions and/or tumors within the mucosal and submucosal layers of the gastrointestinal (GI) tract. To reduce the risk of perforating the GI tract it is important to separate the submucosal layer from the underlying muscularis layer prior to performing the resection or dissection procedure. A common way to establish this separation is to inject a fluid between the muscularis and submucosal tissue layers. Unfortunately, these injected fluids tend to dissipate within the surrounding tissues and therefore may not sufficiently raise or separate the tissue lesion and/or tumor for the entire duration of the procedure. This problem is exacerbated by the tendency of fluid to leak through the incision made by the tissue cutting element during the procedure. While additional fluid may be introduced throughout the procedure, such additional steps may increase procedure times and also create additional injection holes through which the fluid may leak out.

Systems and methods that allow malignant and pre-malignant lesions and/or tumors within the GI tract to remain separated from and elevated above the muscularis layer for the entire duration of the resection or dissection procedure may provide a solid support against which the tissue cutting and manipulating elements may exert force without the need for repeated fluid injections.

SUMMARY

The present disclosure, in its various aspects, delivers an expandable scaffold between tissue layers (e.g., between the muscularis and submucosa layers) to elevate and stabilize malignant and pre-malignant lesions and/or tumors for fast and efficient en bloc resection. The expandable frameworks disclosed herein may be used between any two adjacent tissue layers that require separating and in areas of the body outside of the GI tract (e.g., uterus, bladder etc.).

In one aspect, the present disclosure provides a system for resecting tissue, comprising: a delivery device (e.g., endoscope) comprising a proximal end, distal end and lumen extending therebetween; and an expandable scaffold disposed within the lumen of the delivery device, wherein the expandable scaffold is in a first configuration when inside the lumen of the delivery device and a second configuration when outside the lumen of the delivery device, wherein the second configuration is larger than the first configuration. The expandable scaffold may include a spherical framework, helical coil, aneurysm coil, polymeric particle and/or a foam. The helical coil may include rounded ends to reduce or eliminate tissue perforation. The delivery device may include a sharpened distal end. The expandable scaffold may be formed from a metal including, by way of non-limiting example, platinum, tungsten, titanium, stainless steel, nickel and alloys thereof. The expandable scaffold may be formed from a polymer, including, by way of non-limiting example, an acrylate-based polymer, polyurethane-based polymer, polynorbornene-based polymer and/or polylactide-based polymer. The polymer may be a swellable polymers that expands in the aqueous tissue environment. The foam may be a pre-formed foam or an in-situ forming foam. The system may further include a pushrod slidably disposed within the lumen of the delivery device to push/expel the scaffold from the lumen of the delivery device. The system may further include a cutting element, including, for example, a sharpened edge (e.g., knife, scalpel, scissors etc.) or electrocautery element, slidably disposed within a working channel of the delivery device. When disposed between tissue layers the expandable scaffold may immobilize the tissue and/or provide a firm tissue surface against which the cutting element may act to precisely dissect the tissue lesion and/or tumor.

In another aspect, the present disclosure provides a method for resecting tissue, comprising: positioning a delivery device between adjacent first and second tissue layers, the delivery device comprising: a proximal end, a distal end and a lumen extending therebetween; delivering an expandable scaffold from the lumen of the delivery device into a region between the adjacent first and second tissue layers, wherein the expandable scaffold is in a first configuration when inside the lumen of the delivery device and a second configuration when outside the lumen of the delivery device, wherein the second configuration is larger than the first configuration; and resecting at least a portion of the first tissue layer. The first tissue layer may be lifted and separated from the second tissue layer as the expandable scaffold moves to the second configuration. The first tissue layer may include a submucosal tissue layer and the second tissue layer may include a muscularis tissue layer. The muscularis tissue layer may include a lesion, tumor or other malignant, pre-malignant or potentially malignant tissue. The expandable scaffold may be retracted into the lumen of the delivery device following tissue resection. Alternatively, the scaffold may remain inside the body lumen following tissue resection such that it passes from the lumen in the body's natural course. A fluid may be delivered into a space between the adjacent first and second tissue layers prior to delivering the expandable scaffold. Depending on the size or shape of the tissue lesion, one or more expandable scaffolds may be delivered (i.e., packed) into the region between the adjacent first and second tissue layers.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

Figure 1:
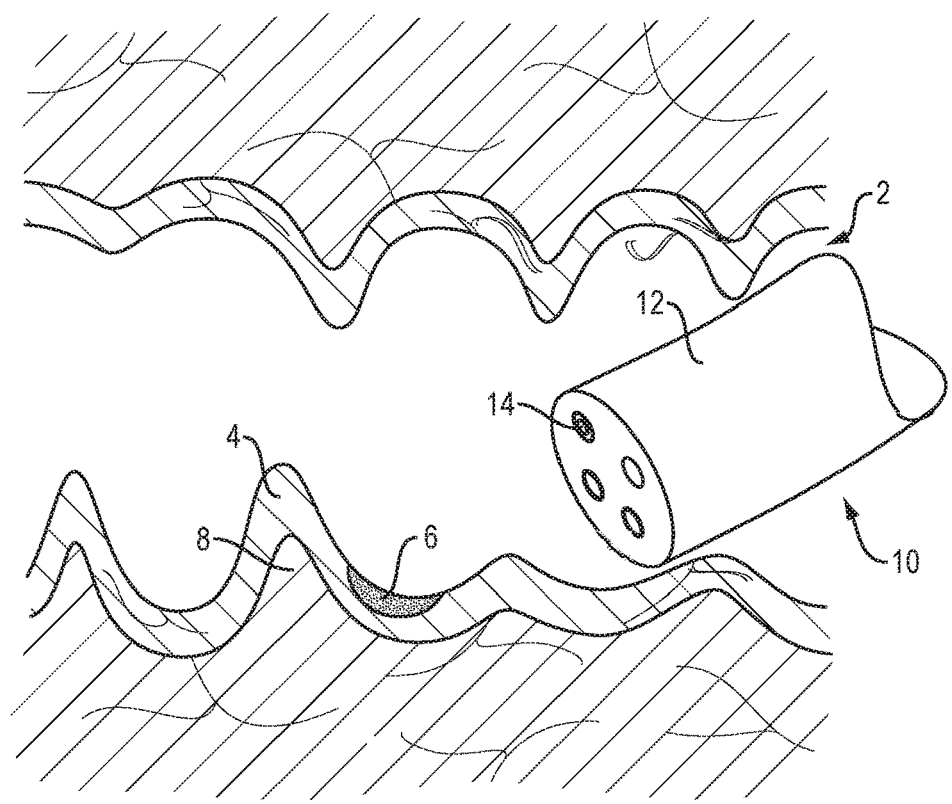
FIG. 1 illustrate a tissue lesion within the submucosal layer of the wall of the GI tract, according to an embodiment of the present disclosure.

It is noted that the drawings are intended to depict only typical or exemplary embodiments of the disclosure. It is further noted that the drawings may not be necessarily to scale. Accordingly, the drawings should not be considered as limiting the scope of the disclosure. The disclosure will now be described in greater detail with reference to the accompanying drawings.

DETAILED DESCRIPTION OF THE PREFERRED EMBODIMENTS

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to the delivery of an expandable scaffold using an endoscope, it should be appreciated that such scaffold may be delivered using a variety of delivery devices that are inserted into a variety of lumens of a patient, including for example, guide lumens, catheters, ports and the like.

As used herein, the term "distal" refers to the end farthest away from a medical professional when introducing a device into a patient, while the term "proximal" refers to the end closest to the medical professional when introducing a device into a patient.

As used herein, the term "expanded" refers to an increase in size, diameter or profile as compared to the size, diameter or profile in an "unexpanded" or "collapsed" configuration.

As used herein, the term "en bloc" refers to the complete or total dissection or resection of a tissue lesion from the surrounding healthy tissue.

As used herein, the terms "resection," dissection" and grammatical equivalents thereof, refers to the removal of a tissue lesion and/or tumor from surrounding heathy tissue using a variety of tissue cutting techniques known in the art. By way of non-limiting example, such cutting techniques may include electrocautery-based tissue cutting elements and/or tissue cutting elements that include sharpened surfaces (i.e., knives, scalpels, scissors and the like).

The present disclosure provides systems and methods for en bloc resection of tissue lesions within the GI tract, including, but not limited to, colorectal cancer lesions of the large bowel. In one aspect, the present disclosure provides various embodiments by which a tissue lesion within the submucosal layer may be lifted and separated from the underlying muscularis layer for safe and efficient resection. While differing in their specific mechanism of action, each embodiment disclosed herein generally includes the following steps: 1) positioning an endoscope within a lumen of a patient adjacent to a tissue lesion, 2) advancing a tissue penetrating device through a working channel of the endoscope such that the sharpened distal end of the tissue penetrating device penetrates the tissue and is positioned between the muscularis and submucosal layers, 3) delivering an expandable scaffold through a lumen of the tissue penetrating device between the muscularis and submucosal layers and underneath at least a portion of the tissue lesion, 4) retracting the tissue penetrating device and allowing the scaffold to move from an unexpanded configuration to an expanded configuration, thereby lifting and separating the submucosal layer and tissue lesion from the underlying muscularis layer and 5) resecting the tissue lesion using a tissue cutting element disposed within a working channel of the endoscope.

When in the expanded configuration the scaffolds described herein exert a radial force which lifts and separates the submucosal layer (and tissue lesion therein) from the underlying muscularis layer to form a protrusion or "bleb." This protrusion improves the physician's ability to visualize the tissue lesion and provides a space or buffer zone to minimize the likelihood of muscularis perforations. The radial force exerted by these non-diffusible expanded scaffolds also place the tissue lesion and surrounding healthy tissue under constant and consistent tension to minimize movement of (i.e., immobilize) the tissue lesion and provide a firm surface against which tissue cutting and tissue manipulating elements may exert force for precise resection along the margins of the tissue lesion. It should be appreciated that the size, shape, number and/or volume of scaffolds delivered between the muscularis and submucosal layers may vary depending on the size and/or shape of the tissue lesion. To this end, multiple scaffolds (or additional volumes of scaffold) may be delivered simultaneously or in succession.

The expandable frameworks disclosed herein may be advanced through the lumen of the tissue penetrating device in a first configuration (i.e., unexpanded or constrained) using a variety of delivery mechanisms known in the art. By way of non-limiting example, the expandable frameworks may be delivered using a pushrod that extends the length of the working channel of the endoscope and includes a distal end which is slidably disposed within the lumen of the tissue penetration device. Alternatively, or in addition, the expandable frameworks may be deployed through the lumen of the tissue penetrating device using a pulse of compressed air or other suitable fluid delivered from a pressurized fluid reservoir located beyond the proximal end of the endoscope.

Figure 7:
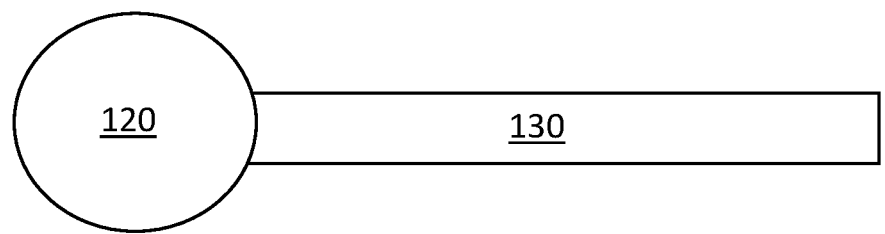
FIG. 7 schematically illustrates a scaffold connected to a delivery wire, according to an embodiment of the present disclosure.

In one embodiment, the scaffolds disclosed herein may be retrieved (i.e., retracted) back through the endoscope following resection of the tissue lesion. For example, the scaffold 120 may be connected to a delivery wire 130 (see FIG. 7) that extends the length of the endoscope working channel. Pulling/retracting a proximal end of the delivery wire in a proximal direction may force the expanded scaffold to return to the unexpanded configuration as it re-enters the lumen of the tissue penetrating device. The delivery wire may also be used to maintain a force on the expandable scaffold during the tissue resecting procedure to prevent the scaffold from "jumping" or "springing" free as the muscularis layer is compromised by the tissue cutting element. Alternatively, the scaffold may be retrieved in the expanded configuration through a separate (i.e., larger diameter) working channel of the endoscope. In another embodiment, the scaffold may remain within the lumen of the GI tract in the expanded configuration to be passed by the body's natural course.

Although the embodiments described herein address the problems associated with existing techniques which rely on injected fluids to lift and separate adjacent tissue layers, it should be appreciated that the expandable scaffolds disclosed herein may be used in conjunction with such fluid injections. For example, the scaffold may be introduced along with (i.e., simultaneous to) a fluid. Alternatively, the scaffold may be introduced into a pre-formed "bleb" created by a volume of fluid injected between the muscularis and submucosal layers.

Finally, the expandable frameworks, such as helical coils and/or aneurysm coils disclosed herein may be formed from resilient inert materials, including metals and metal alloys such as platinum, tungsten, titanium, stainless steel, nickel and nickel-titanium alloys (e.g., nitinol), polymers such as acrylate-based polymers, polyurethane-based polymers, polynorbornene-based polymers, and polylactide-based polymers, and any combinations thereof. Other examples of polymers are disclosed, for example, in Buiser et al., U.S. Patent Pub. No. 20070141099, which is incorporated herein by reference. These materials may be coated with insulating substances to minimize or eliminate electrical conductivity. FIG. 1 generally depicts an endoscope 10 positioned within the lumen 2 of the GI tract adjacent to a tissue lesion 6 within the submucosal layer 4. The endoscope 10 may include a distal end 12, a proximal end (not shown) and a working channel (not shown) extending therebetween. The distal end 12 of the endoscope 10 may include a camera 14 to visualize the working area and assist the physician in navigating the tortious anatomy of the GI tract. A variety of extendable/retractable medical instruments, including, for example, a tissue penetrating device 16 and/or a tissue cutting element 18 (e.g., FIG. 2C) may extend through the working channel to manipulate tissues beyond the distal end of the endoscope. As evidenced by the proximity of the tissue lesion 6 to the muscularis layer 8, it will be appreciated that en bloc resection of the tissue lesion 6 without lifting and separating the submucosal layer 4 from the underlying muscularis layer 8 would be extremely difficult, time consuming and present a high likelihood of muscularis perforation.

Figure 2A:
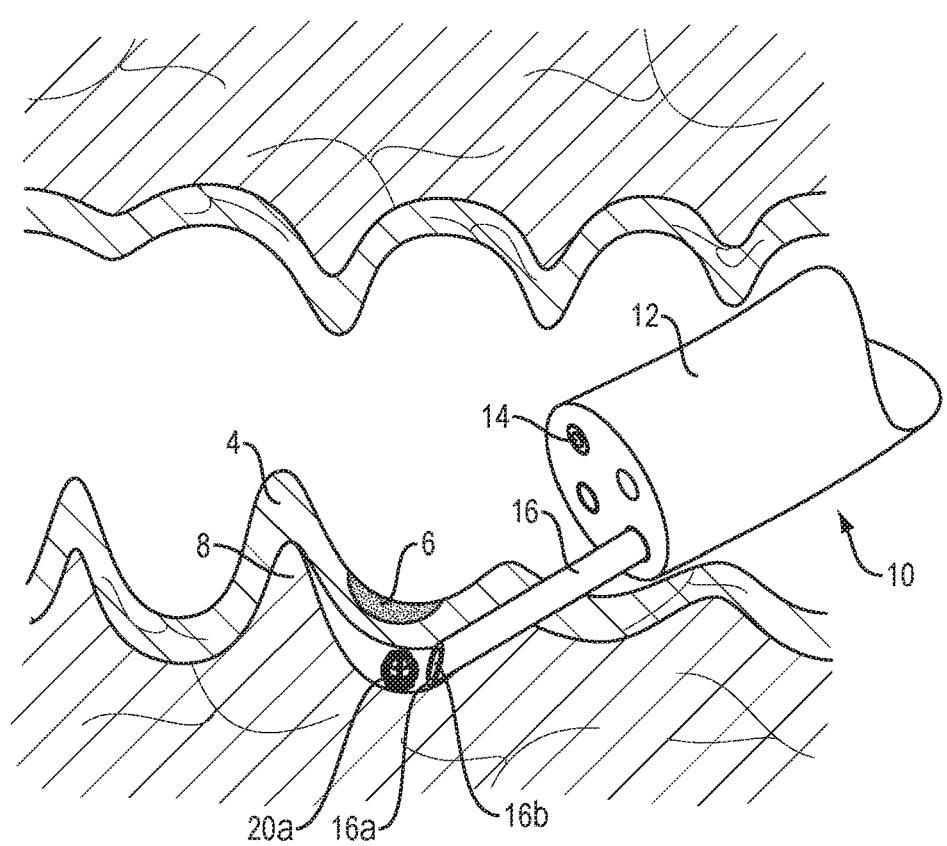
FIGS. 2A-C illustrate resecting a tissue lesion by introducing an expandable framework between the muscularis and submucosal tissue layers, according to an embodiment of the present disclosure.
Figure 2B:
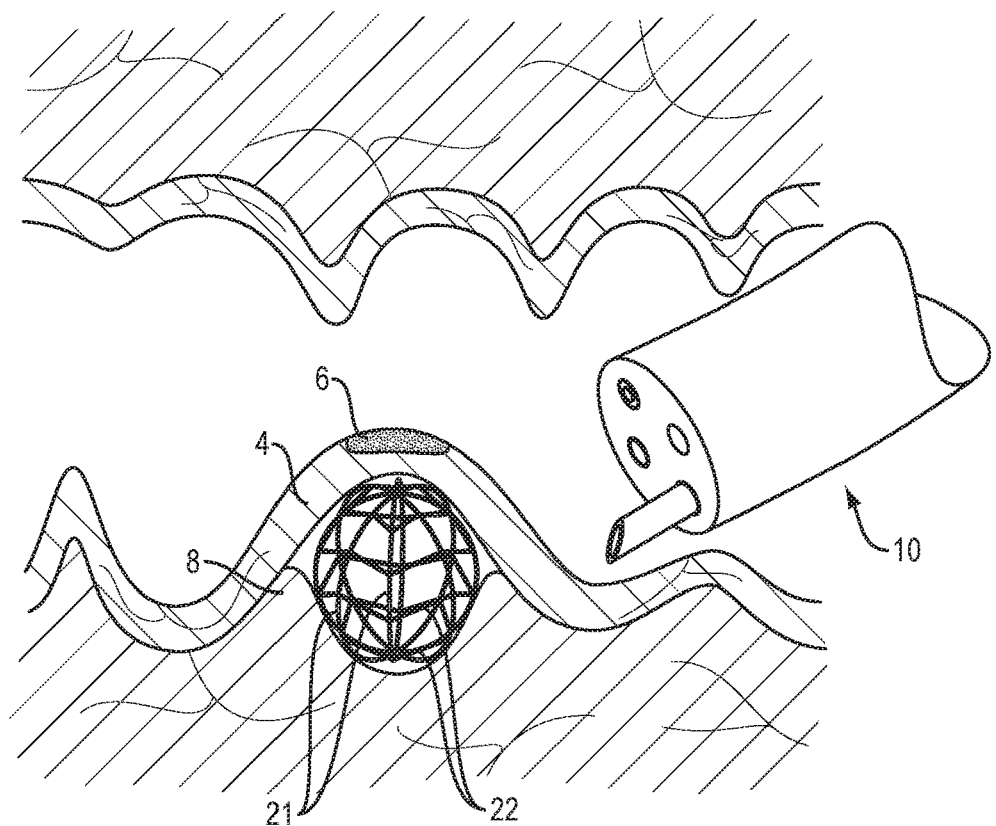

Referring to FIG. 2A, the endoscope 10 may be advanced through the lumen 2 of the GI tract such that the distal end 12 of the endoscope is adjacent to a tissue lesion 6. A tissue penetrating device 16 (i.e., injection needle, syringe etc.) that includes a sharpened distal end 16a may be advanced beyond the distal end of the endoscope and through the submucosal layer 4 such that the sharpened distal end 16a of the tissue penetrating device 16 is positioned between the muscularis and submucosal layers 8, 4. The tissue penetrating device may include a lumen 16b through which an expandable framework 20 may be deployed. When the expandable framework 20 is no longer constrained within the lumen of the tissue penetrating device it moves from the first (unexpanded) configuration 20a to the second (expanded) configuration, thereby lifting and separating the submucosal layer 4 from the underlying muscularis layer 8 (FIG. 2B). A tissue cutting element 18 may then be deployed through the working channel of the endoscope 10 to resect the tissue lesion 6 along its margins (FIG. 2C), as discussed above.

Figure 2C:
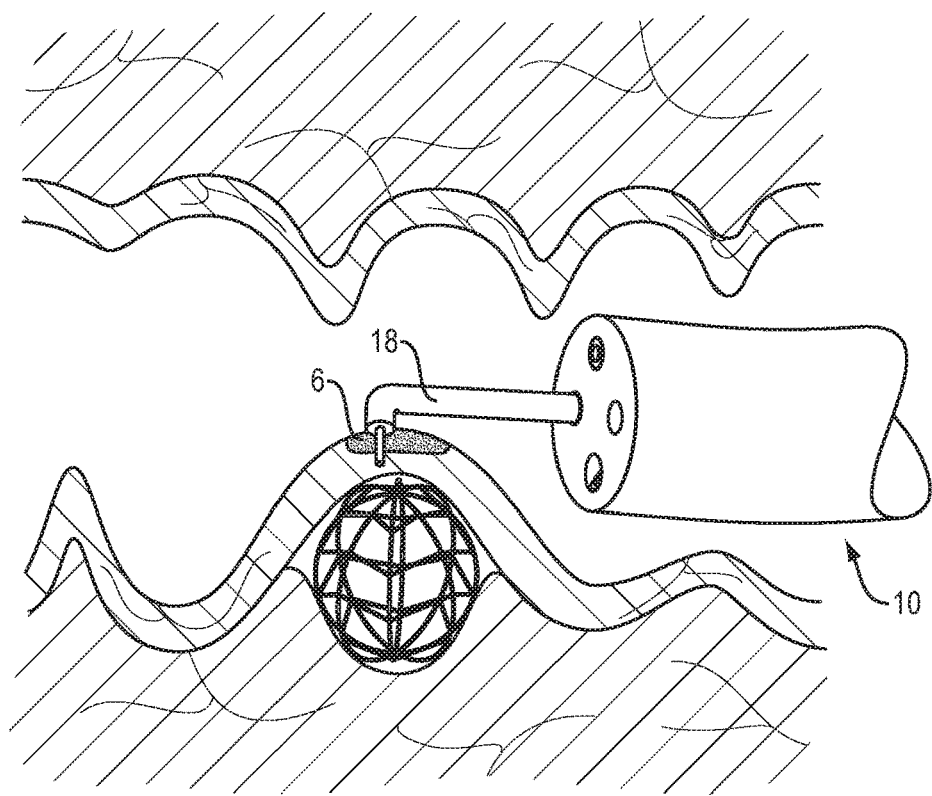

As depicted in FIG. 2B, in one embodiment the expandable framework 20 may include a substantially spherical shape formed by a plurality of flexible curved longitudinal members 21 (i.e., flexible splines) which extend in a circumferentially spaced relationship. These splines may include regions of varying flexibility and/or stiffness such that the expandable framework separates the respective tissue layers when in the expanded configuration. Adjacent longitudinal members 21 may be connected by a series of cross-pieces 22 (i.e., struts) to form a mesh- or basket-like structure with sufficient structural integrity to maintain a constant radial force on the muscularis layer. It should be appreciated that while the expandable framework depicted in FIGS. 2A-C is generally spherical in shape, the present disclosure may include a variety of symmetrical or non-symmetrical expandable framework configurations, as are known in the art.

Figure 3A:
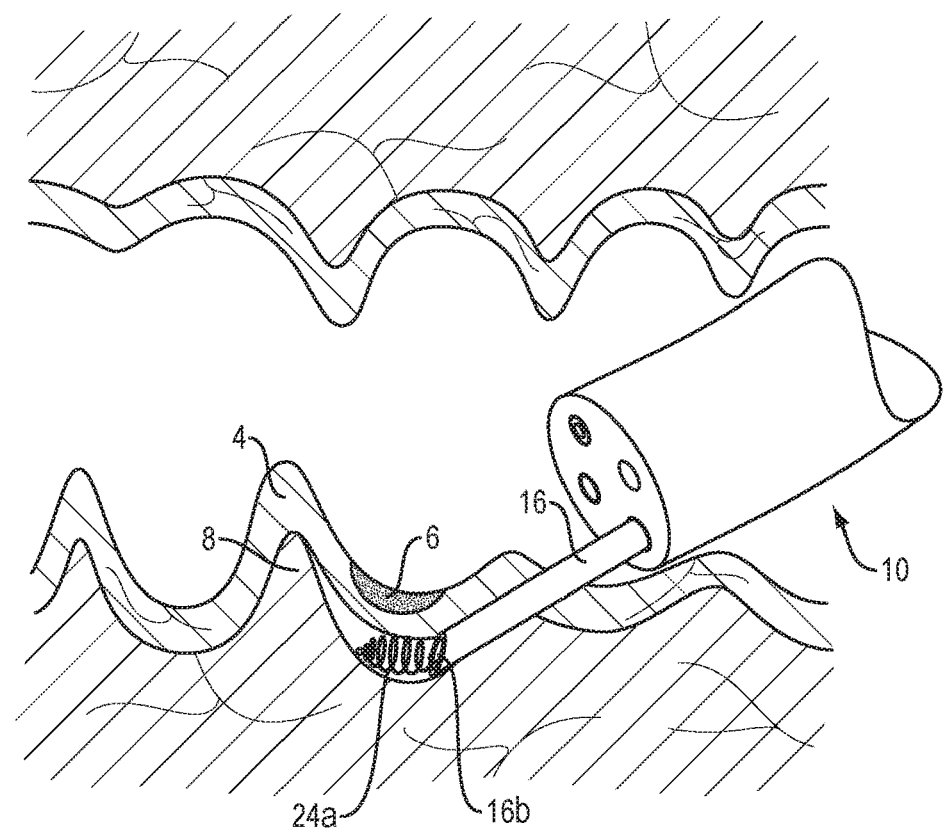
FIGS. 3A-C illustrate resecting a tissue lesion by introducing an expandable helical coil between the muscularis and submucosal tissue layers, according to an embodiment of the present disclosure.
Figure 3B:
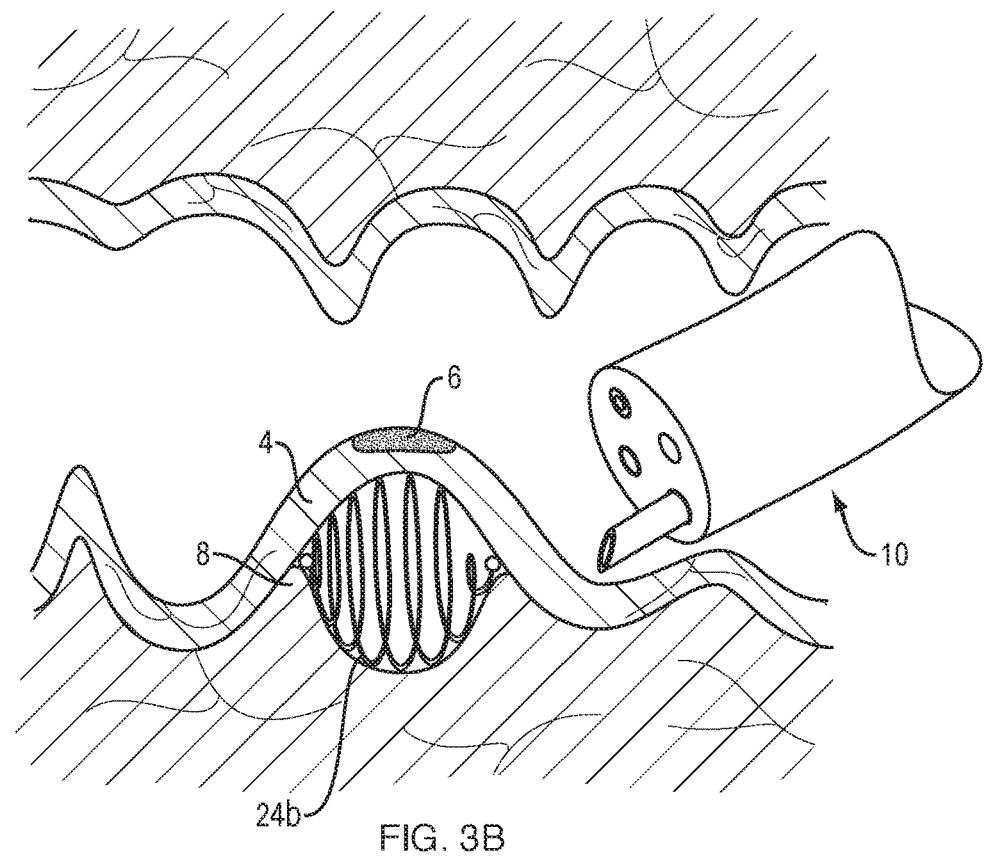
Figure 3C:
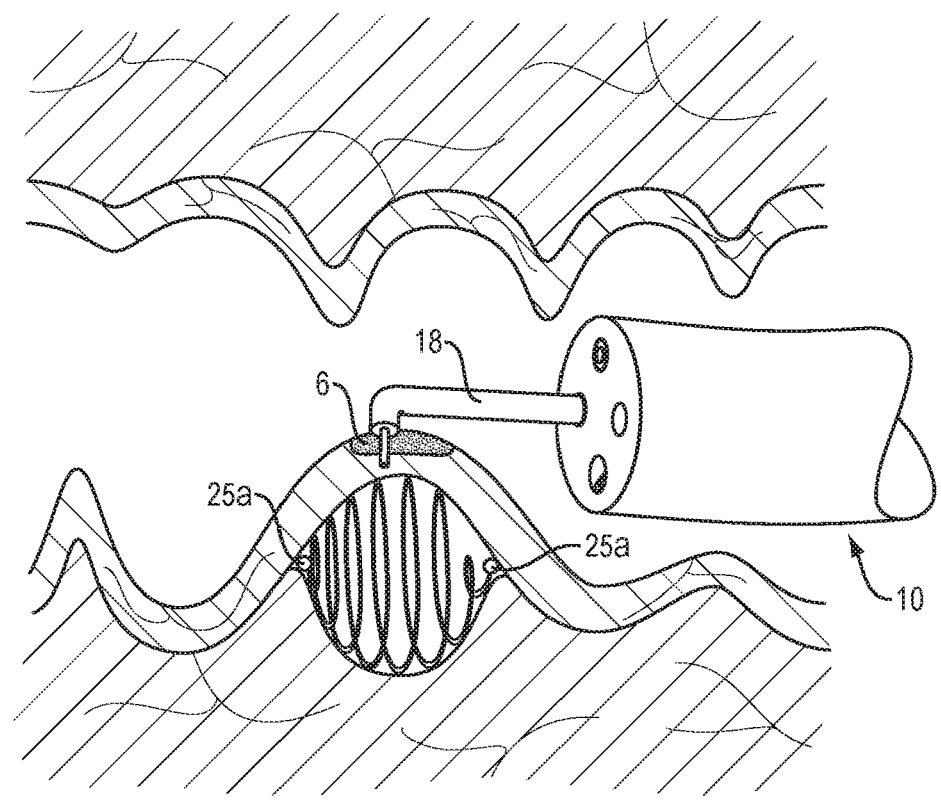

Referring to FIG. 3A, in one embodiment the expandable scaffold may include a coil formed from a shape memory material that includes a helical bias. The helical coil 24 may be delivered in a first (unexpanded) configuration 24a through the lumen 16b of the tissue penetrating device 16 into the region between the submucosal 4 and muscularis 8 tissue layers. When the helical coil 24 is no longer constrained within the lumen of the tissue penetrating device it moves from the first (unexpanded) configuration 24a to the second (expanded) configuration 24b, thereby lifting and separating the submucosal layer 4 from the underlying muscularis layer 8 (FIG. 3B). A tissue cutting element 18 may then be deployed through a working channel of the endoscope 10 to resect the tissue lesion 6 along its margins (FIG. 3C), as discussed above. To reduce the risk of submucosal perforation, the helical coil 24 may include rounded ends 25a, including, by way of non-limiting example, mechanically formed structures (i.e., balls etc.) attached by welding, soldering, adhesives and the like.

The relative stiffness of the expandable helical coil may depend, among other things, on its composition, the diameter of the wire strand, the diameter of the mandrel around which it is wound and the pitch of the primary windings.

Figure 4A:
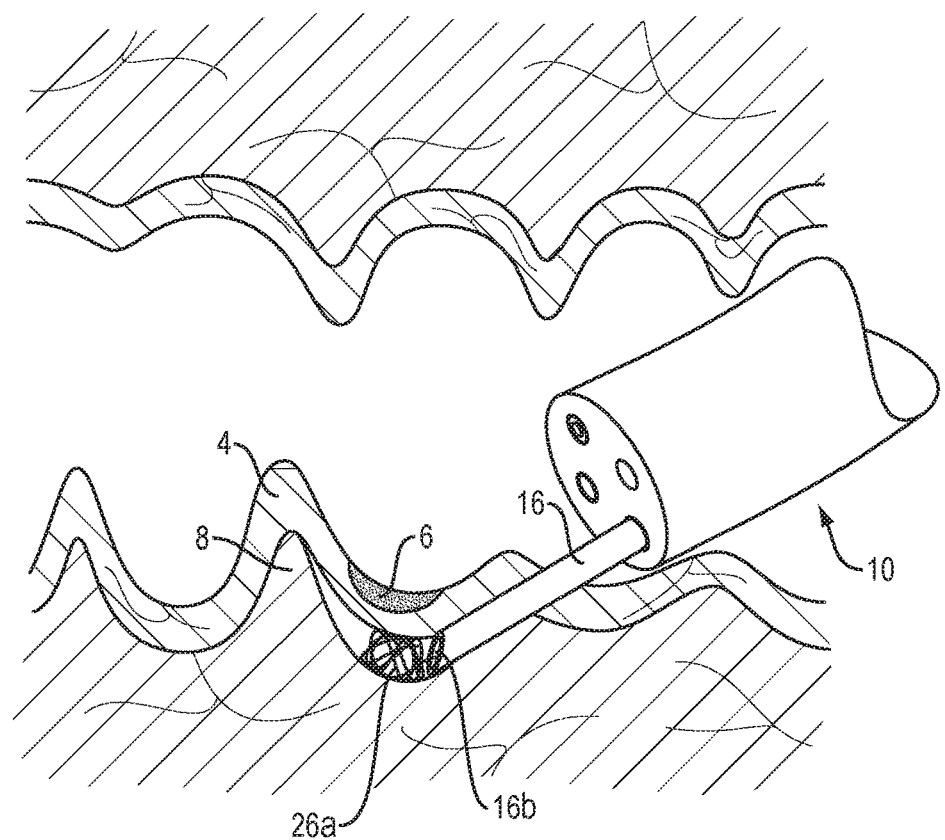
FIGS. 4A-C illustrate resecting a tissue lesion by introducing an aneurysm coil between the muscularis and submucosal tissue layers, according to an embodiment of the present disclosure.
Figure 4B:
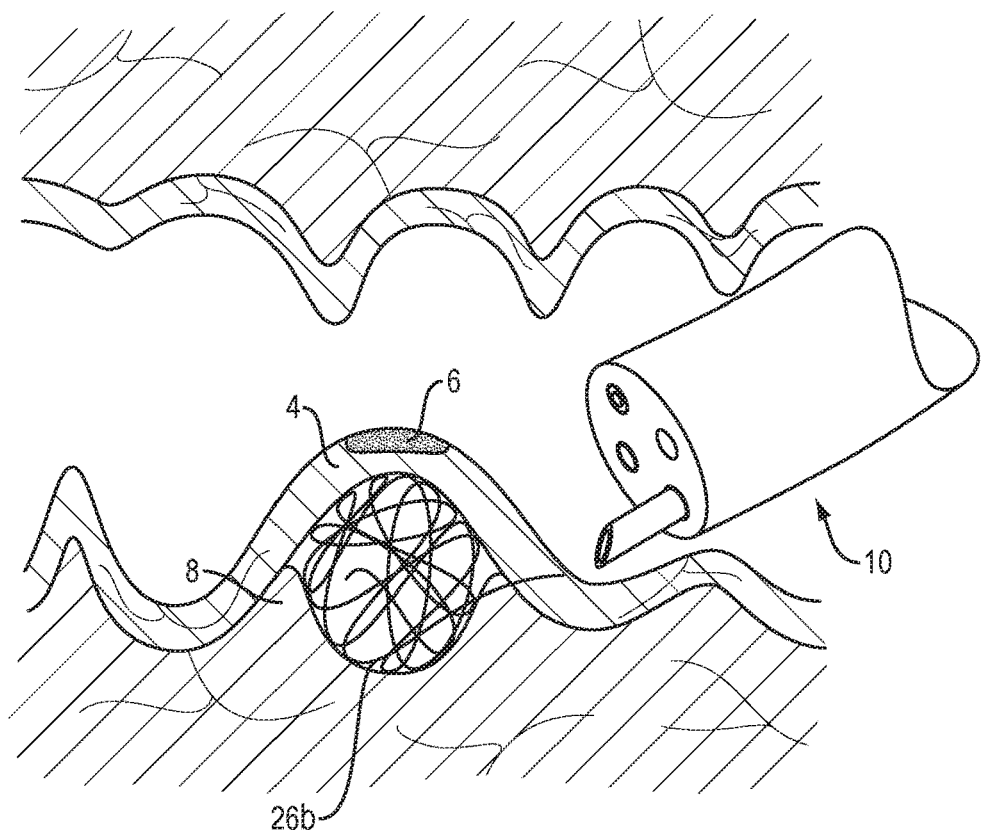
Figure 4C:
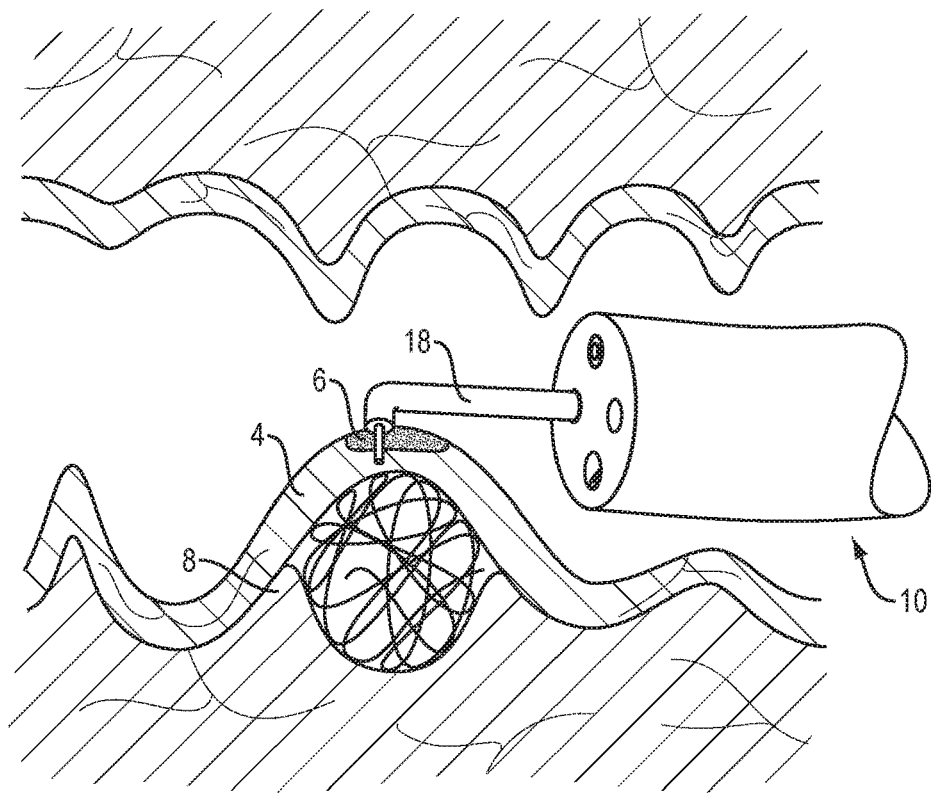

Referring to FIG. 4A, in one embodiment the expandable scaffold may include an aneurysm coil 26 formed from a shape memory material. The aneurysm coil may be delivered in a first (linear) configuration 26a through the lumen 16b of the tissue penetrating device 16 into the region between the submucosal 4 and muscularis 8 tissue layers. As the aneurysm coil 26 exits the lumen of the tissue penetrating device it moves from the first (linear) configuration 26a to a second (grid or matrix-like) configuration 26b, thereby lifting and separating the submucosal layer 4 from the underlying muscularis layer 8 (FIG. 4B). In one embodiment, a proximal end of the aneurysm coil (not shown) may be connected to a torsionally rigid member (e.g., pushrod or string etc.; not shown) that allows the physician to pack or compress the aneurysm coil within the space between the muscularis and submucosal layers to achieve a desired coil density. A tissue cutting element 18 may be deployed through a working channel of the endoscope to resect the tissue lesion 6 along its margins (FIG. 4C), as discussed above.

Figure 5A:
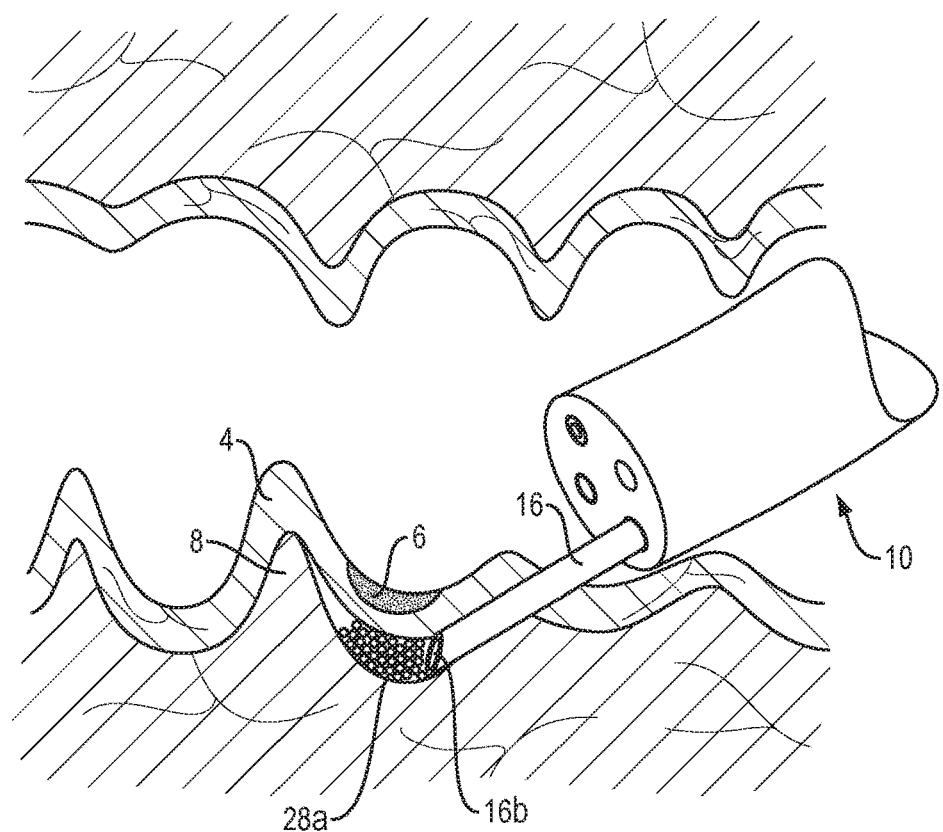
FIGS. 5A-C illustrate resecting a tissue lesion by introducing swellable polymeric particles between the muscularis and submucosal tissue layers, according to an embodiment of the present disclosure.
Figure 5B:
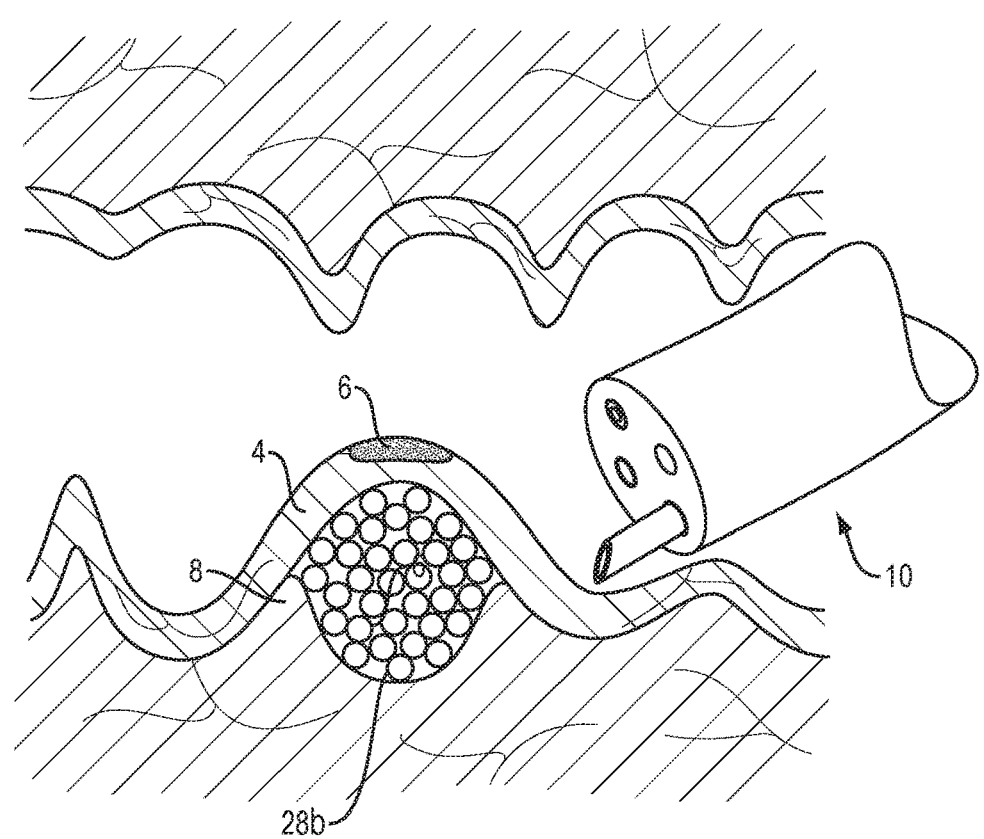
Figure 5C:
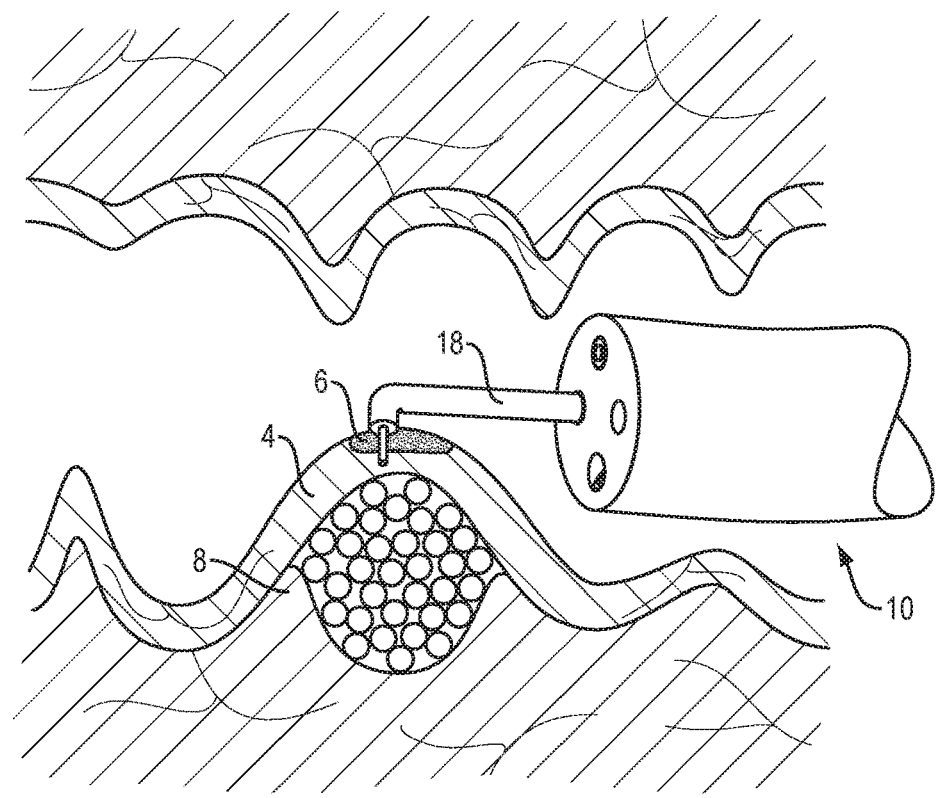

Referring to FIG. 5A, in one embodiment the expandable scaffold may include a plurality of polymeric particles 28 which expand/swell in the presence of an aqueous environment. It should be appreciated that the expandable and/or swellable polymeric particles 28 may include a variety of shapes (e.g., spheres etc.), sizes and materials (e.g., polypropylenes, polyacrylics and the like). As the polymeric particles 28 exit the lumen 16*b* of the tissue penetrating device 16 they absorb moisture and swell/expand from a first (unexpanded) configuration 28*a* to a second (expanded) configuration 28*b*, thereby lifting and separating the submucosal layer 4 above the muscularis layer 8 (FIG. 5B). In one embodiment, the polymeric particles may swell/expand by absorbing moisture within (and between) the mucosal and submucosal tissue layers. In addition, or alternatively, a biologically compatible fluid (e.g., sterile saline) may be introduced through the lumen of the tissue penetrating device along with the polymeric particles to provide the requisite aqueous environment for expansion. A tissue cutting element 18 may then be deployed through a working channel of the endoscope to resect the tissue lesion along its margins (FIG. 5C), as discussed above.

Figure 6A:
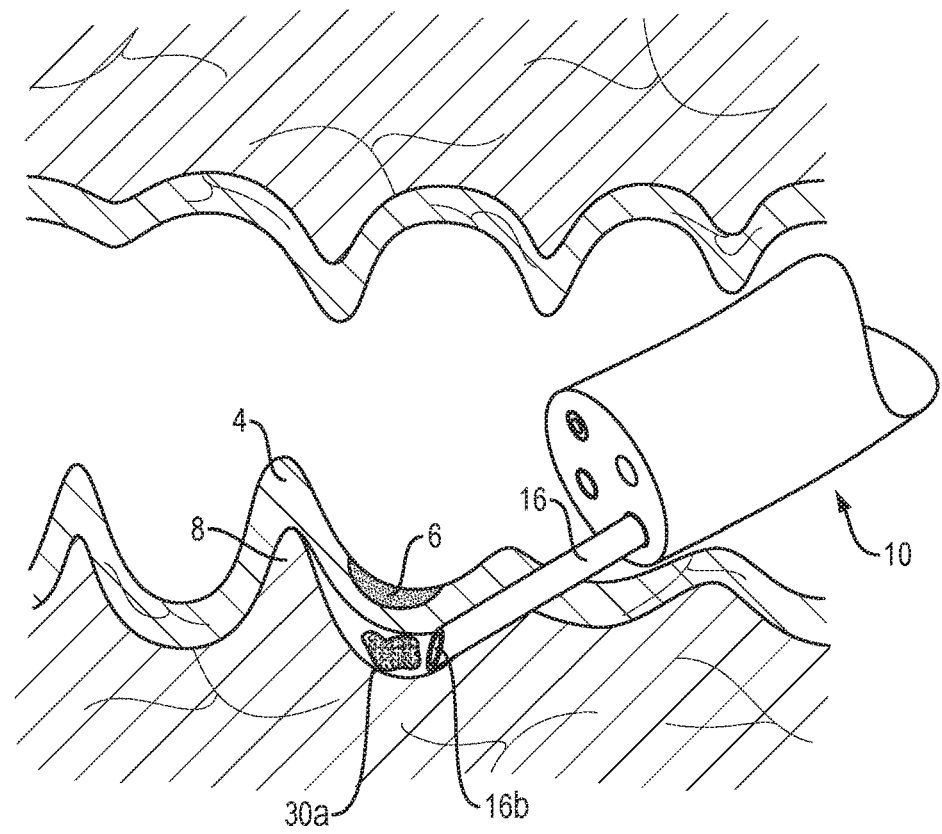
FIGS. 6A-C illustrate resecting a tissue lesion by introducing an expandable foam between the muscularis and submucosal tissue layers, according to an embodiment of the present disclosure.
Figure 6B:
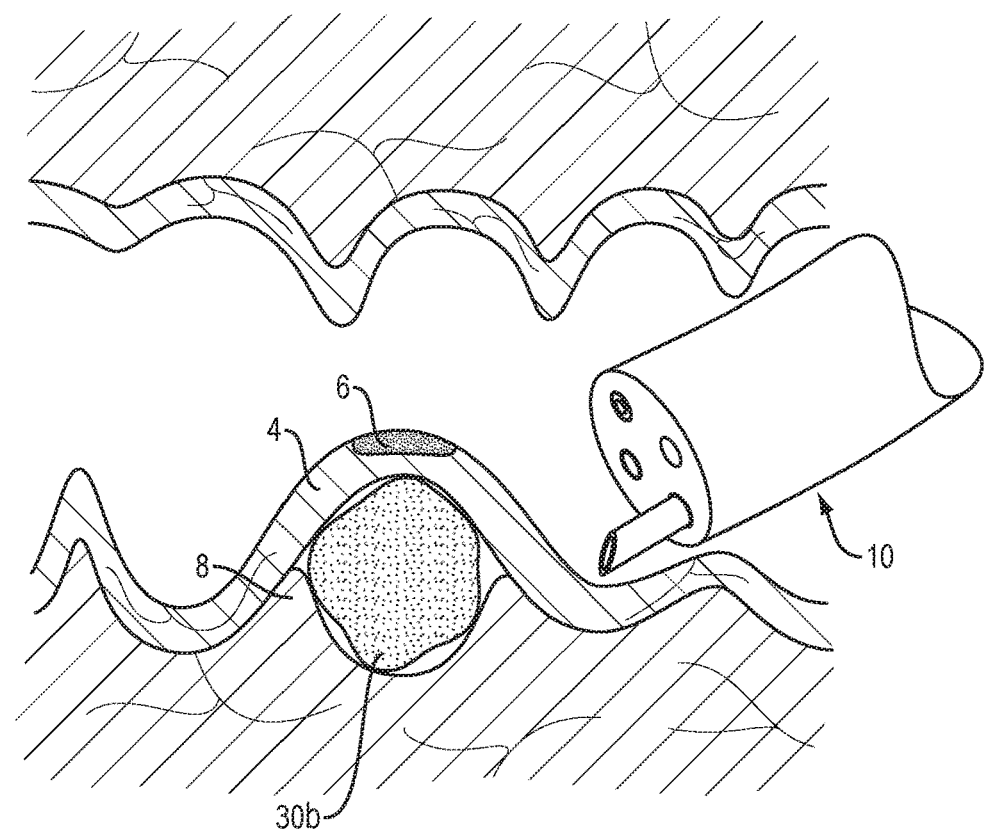

Referring to FIG. 6A, in one embodiment the expandable scaffold may include an expandable foam 30. In one embodiment, the expandable foam 30 may include a preformed foam that is maintained in the first (unexpanded) configuration 30*a* within the lumen of the tissue penetrating device. As a pre-determined amount of the pre-formed foam is delivered from the lumen 16*b* of the tissue penetrating device 16 it moves from the first (unexpanded) configuration 30*a* to the second (expanded) configuration 30*b*, thereby lifting and separating the submucosal layer 4 from the underlying muscularis layer 8 (FIG. 6B). A tissue cutting element 18 may then be deployed through a working channel of the endoscope to resect the tissue lesion 6 along its margins (FIG. 6C), as discussed above.

Figure 6C:
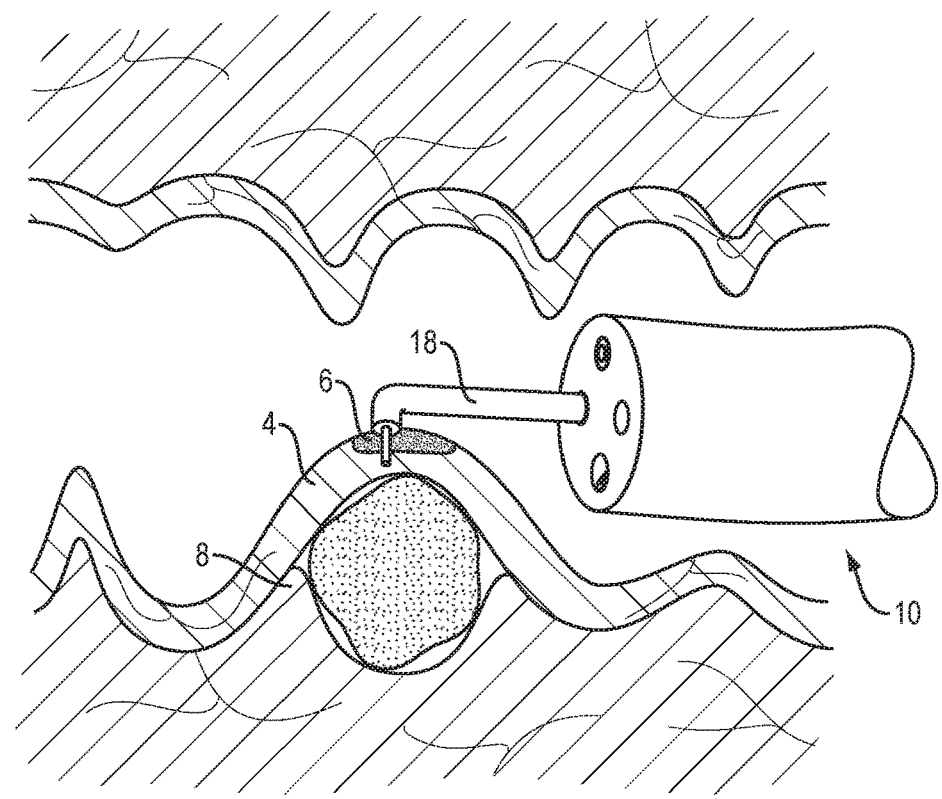

Referring again to FIG. 6A, in another embodiment, the expandable foam 30 may include a liquid foam precursor 30 that undergoes a chemical reaction in the presence of an aqueous environment to assume the expanded configuration 30*b*. The chemical reaction may be facilitated by the moisture present within (and between) the mucosal and submucosal tissue layers. In addition, or alternatively, a biologically compatible fluid (e.g., sterile saline) may be introduced along with the liquid foam precursor 30 to provide the requisite aqueous environment for the chemical reaction to proceed. Alternatively, the liquid foam precursor 30 may be administered along with a compressed biologically inert gas that forms bubbles within the liquid foam which facilitate expansion of the foam. As a pre-determined amount of the liquid foam precursor 30 is delivered from the lumen of the tissue penetrating device it moves from the first (unexpanded) configuration 30*a* to the second (expanded) configuration 30*b*, thereby lifting and separating the submucosal layer 4 from the underlying muscularis layer 8 (FIG. 6B). As above, a tissue cutting element 18 may then be deployed through a working channel of the endoscope to resect the tissue lesion 6 along its margins (FIG. 6C).

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for resecting tissue, comprising:
    a tissue penetrating delivery device comprising a proximal end, distal end and a lumen extending therebetween, wherein the distal end is configured to be positioned between adjacent first and second tissue layers, wherein the first tissue layer includes a submucosal tissue layer and the second tissue layer includes a muscularis tissue layer;
    a self-expandable scaffold disposed within the lumen of the tissue penetrating delivery device and configured to be deployed between the first and second tissue layers, wherein the self-expandable scaffold is in a first configuration when inside the lumen of the tissue penetrating delivery device and a second configuration when deployed between the first and second tissue layers, wherein the second configuration is larger than the first configuration to separate the first and second tissue layers; and
    an additional instrument comprising a tissue cutting element configured to resect at least a portion of the submucosal tissue layer;
    wherein the scaffold is connected to a delivery wire that is configured to retrieve the scaffold following resection of the tissue by pulling a proximal end of the delivery wire in a proximal direction to withdraw the scaffold into the lumen of the tissue penetrating device.

2. The system of claim 1, wherein the tissue penetrating delivery device includes a sharpened distal end.

3. A method for resecting tissue using the system of claim 1, comprising:
    positioning the distal end of the delivery device between the adjacent first and second tissue layers;
    delivering the self-expandable scaffold from the lumen of the delivery device into a region between the adjacent first and second tissue layers, wherein the self-expandable scaffold expands to the second configuration, lifting and separating the adjacent first and second tissue layers; and
    resecting at least a portion of the first tissue layer using the tissue cutting element.

4. The method of claim 3, wherein the muscularis tissue layer includes a lesion.

5. The method of claim 4, wherein the lesion is a malignant or pre-malignant lesion.

6. The method of claim 3, wherein the self-expandable scaffold is retracted into the lumen of the delivery device following tissue resection.

7. The method of claim 3, wherein a fluid is delivered into a space between the adjacent first and second tissue layers prior to delivering the self-expandable scaffold.

8. The system of claim 1, wherein the tissue cutting element includes a sharpened edge or an electrocautery element.

9. The system of claim 1, wherein the system further comprises an endoscope having a working channel and wherein the tissue cutting element is configured to be slidably disposed within the working channel.

10. The system of claim 1, further comprising a fluid, the system being configured to introduce the fluid through the lumen and between the submucosal tissue layer and the muscularis tissue layer either prior to or simultaneously with the scaffold.

11. The system of claim 1, wherein the self-expandable scaffold is formed from a shape memory material.

12. The system of claim 1, wherein the self-expandable scaffold is formed into a sphere or a coil.

13. The system of claim 1, further comprising an endoscope having a proximal end and a distal end, wherein the tissue penetrating delivery device and the additional instrument comprising a tissue cutting element are configured to extend through a working channel of the endoscope to manipulate tissues beyond the distal end of the endoscope.

14. A system for resecting tissue, comprising:
a tissue penetrating delivery device comprising a proximal end, distal end and a lumen extending therebetween, wherein the distal end is configured to be positioned between adjacent first and second tissue layers, wherein the first tissue layer includes a submucosal tissue layer and the second tissue layer includes a muscularis tissue layer;
an expandable scaffold disposed within the lumen of the tissue penetrating delivery device and configured to be deployed between the first and second tissue layers, wherein the expandable scaffold is in a first configuration when inside the lumen of the tissue penetrating delivery device and a second configuration when deployed between the first and second tissue layers, wherein the second configuration is larger than the first configuration to separate the first and second tissue layers; and
an additional instrument comprising a tissue cutting element configured to resect at least a portion of the submucosal tissue layer;
wherein the scaffold is in the form of a helical coil that comprises rounded ends that resist tissue perforation;
wherein the scaffold is connected to a delivery wire that is configured to retrieve the scaffold following resection of the tissue by pulling a proximal end of the delivery wire in a proximal direction to withdraw the scaffold into the lumen of the tissue penetrating device.

15. The system of claim 14, wherein the tissue cutting element includes a sharpened edge or an electrocautery element.

16. The system of claim 14, wherein the system further comprises an endoscope having a working channel and wherein the tissue cutting element is configured to be slidably disposed within the working channel.

17. The system of claim 14, further comprising a fluid, the system being configured to introduce the fluid through the lumen and between the submucosal tissue layer and the muscularis tissue layer either prior to or simultaneously with the scaffold.

* * * * *